(12) United States Patent
Varughese Chacko et al.

(10) Patent No.: US 12,329,454 B2
(45) Date of Patent: Jun. 17, 2025

(54) BINOCULAR OPTICAL COHERENCE TOMOGRAPHY IMAGING SYSTEM

(71) Applicant: OPTOS PLC, Dunfermline (GB)

(72) Inventors: Lijo Varughese Chacko, Dunfermline (GB); Margaret Catherine Normand, Dunfermline (GB)

(73) Assignee: OPTOS PLC, Dunfermline (GB)

( * ) Notice: Subject to any disclaimer, the term of this patent is extended or adjusted under 35 U.S.C. 154(b) by 988 days.

(21) Appl. No.: 17/339,980

(22) Filed: Jun. 5, 2021

(65) Prior Publication Data
US 2022/0015624 A1 Jan. 20, 2022

(30) Foreign Application Priority Data

Jul. 17, 2020 (EP) .................................... 20186520

(51) Int. Cl.
*A61B 3/10* (2006.01)
*A61B 3/00* (2006.01)
*G01B 9/02091* (2022.01)

(52) U.S. Cl.
CPC ............ *A61B 3/102* (2013.01); *A61B 3/0058* (2013.01); *A61B 3/1025* (2013.01); *G01B 9/02091* (2013.01)

(58) Field of Classification Search
CPC ..... A61B 3/102; A61B 3/0058; A61B 3/1025; G01B 9/02091

(Continued)

(56) References Cited

U.S. PATENT DOCUMENTS

| 2010/0110377 A1* | 5/2010 | Maloca | A61B 3/102 351/208 |
| 2016/0252340 A1* | 9/2016 | Hollenbeck | G01B 9/02004 356/479 |

(Continued)

FOREIGN PATENT DOCUMENTS

| JP | 2015-114284 | 6/2015 |
| JP | 2016-505828 | 2/2016 |

(Continued)

OTHER PUBLICATIONS

Notice of Reasons for Rejection drafted Jul. 26, 2022 in Japanese patent application No. 2021-116377 (2 sheets). (English translation attached: 2 sheets).

(Continued)

*Primary Examiner* — Sharrief I Broome
(74) *Attorney, Agent, or Firm* — FAEGRE DRINKER BIDDLE & REATH

(57) ABSTRACT

A binocular OCT imaging system for simultaneously imaging regions of a first eye and second eye using an interferometer having a reference arm, first sample arm and second sample arm, by: obtaining an electrical signal (S) having first frequency components spanning a first band and caused by interference between reference light in the reference arm with light reflected from the first eye in the first sample arm, and second frequency components spanning a second band and caused by interference between the reference light and light reflected from the second eye in the second sample arm; and generating OCT images of: the region of the first eye using first frequency components in a portion of the first band not overlapping the second band; and the region of the second eye using second frequency components in a portion of the second band not overlapping the first band.

10 Claims, 10 Drawing Sheets

(58) Field of Classification Search
USPC .......................................................... 351/206
See application file for complete search history.

(56) References Cited

U.S. PATENT DOCUMENTS

| | | | | |
|---|---|---|---|---|
| 2017/0311796 | A1* | 11/2017 | Walsh | A61B 3/0058 |
| 2019/0059720 | A1* | 2/2019 | Kubota | A61B 3/0025 |
| 2019/0090733 | A1 | 3/2019 | Walsh et al. | |

FOREIGN PATENT DOCUMENTS

| | | | |
|---|---|---|---|
| JP | 2016-536075 | A | 11/2016 |
| WO | 2015023547 | A1 | 2/2015 |
| WO | 2014-088650 | A1 | 6/2016 |

OTHER PUBLICATIONS

European Search Report issued in European patent application No. 20 18 6520.1-1122 (Jan. 21, 2021).

The Explore Study—The Use of Binocular OCT Imaging for the Assessment of Ocular Disease Clinical Trials.gov Identifier NCT03553017, Sponsor: University College, London (first posted Jun. 12, 2018) (7 sheets) (available at https://clinicaltrials.gov/ct2/show/NCT03553017) (printed Jun. 26, 2021).

* cited by examiner

BINOCULAR OPTICAL COHERENCE TOMOGRAPHY IMAGING SYSTEM

CROSS REFERENCE TO RELATED APPLICATION

This application claims the benefit of priority based on European Patent Application EP 20 186 520.1 filed Jul. 17, 2020, the entirety of which is incorporated by reference as if set forth fully herein.

TECHNICAL FIELD

Example aspects herein generally relate to the field of ophthalmic optical coherence tomography (OCT) imaging systems and, more particularly, to binocular OCT imaging systems for imaging both eyes of a subject.

BACKGROUND

Optical coherence tomography provides a powerful tool for examining and assessing the health of an eye. In a swept source OCT (SS-OCT) imaging system, a tunable light source with a narrow linewidth has the optical frequency of its light rapidly swept across a broad spectral bandwidth, and an interference signal is detected by a photodetector of the SS-OCT imaging system as a function of the frequency.

FIG. 1 is a schematic illustration of a conventional ophthalmic SS-OCT imaging system having an interferometer which comprises a swept light source 10 a beam splitter 20, a reference mirror 30, a scanning element 40, and a photodetector 50. A light beam generated by the swept light source 10 is split into two beams by the beam splitter 20, with a first of the beams being guided along a reference arm of the interferometer to the reference mirror 30, and a second of the beams is guided along a sample arm of the interferometer towards an eye 70 of a subject. The scanning element 40 is controlled to direct a light beam 80 in the sample arm to a target scan region 90 of the eye 70, and guide backscattered light from the eye 70 back into the interferometer. The back-reflected light travelling along the reference arm and the backscattered light travelling along the sample arm are then combined at the photodetector 50 to generate an interference light signal. Specifically, interference is observed only when the optical path lengths differ by less than the coherence length of the light source, a quantity that is inversely proportional to its optical bandwidth. The wavelength of the light produced by the swept light source 10 (which is typically provided in the form of a tunable laser or other light source having a narrow linewidth) is rapidly swept over a range of wavelengths for each scan location in the target scan region 90, and the generated interference light signal is detected by the photodetector 50 during the sweep. As the detector 50, a balanced photodiode may be used to increase the signal-to-noise of detection. The output of the photodetector 50, i.e. an interferogram, as schematically illustrated in FIG. 2A, is sampled by a sample acquisition module (not illustrated), and an inverse Fourier transform of the sampled electric signal is then calculated to obtain A-scan data, which provides information on the structure of the target scan region 90 of the eye retina in a depth direction of the region 90. An A-scan can thus be acquired using a single wavelength sweep, for each scan location in the target scan region 90.

FIG. 2A illustrates the interferogram generated by the photodetector 50 of the ophthalmic SS-OCT imaging system in FIG. 1. The horizontal axis in the interferogram represents time (and is also representative of the wavenumber of the light from the light source 10), while the vertical axis represents the power of the interference light signal detected by the photodetector 50. For an interferogram having a single frequency signal (corresponding to interference caused by, for example, a single retinal layer), the frequency of the interferogram is proportional to a product of the wavelength sweep rate of the swept light source 10 and the optical path difference between the reference arm and the sample arm. FIG. 2B schematically illustrates a variation of intensity of the detected interference light as a function of depth along the target scan region 90 that is obtained by performing an inverse Fourier transform on the samples of the interferogram in FIG. 2A.

The example interferogram in FIG. 2A and the example depth profile plot in FIG. 2B are derived from reflections from a single layer within the target scan region 90 of the eye 70. More generally, light scattered from multiple layers at different respective depths within the eye 70 will interfere with the light in the reference arm, and the resulting interferogram will consequently comprise multiple frequency components, each frequency component corresponding to scattered light from a respective layer. In this case, the corresponding depth profile obtained from the interferogram may contain a plurality of peaks, one for each layer that contributed backscattered light to the interference light signal.

SUMMARY

Most current OCT imaging systems capture an OCT image of one eye at a time. After the eye has been imaged, the patient typically has to align their other eye with the OCT imaging system for imaging, and this results in a slow overall imaging acquisition process. In addition, existing binocular OCT imaging systems that are capable of simultaneously capturing OCT images of both eyes require a duplication of imaging hardware for each eye to achieve this functionality, resulting a high imaging system cost.

In view of the above-identified problems, the present inventors have recognised that the long coherence length of a swept light source used in a swept source OCT imaging system can be exploited to devise a binocular OCT imaging system that is capable of imaging both eyes in one single OCT capture using fewer components than conventional binocular OCT imaging systems of the kind mentioned above and, in particular, using a single photodetector and a single reference arm.

More specifically, the present inventors have devised, in accordance with a first example aspect herein, a binocular optical coherence tomography, OCT, imaging system for simultaneously imaging a region of a first eye of a subject and a region of a second eye of the subject. The binocular OCT imaging system comprises a swept light source, which is arranged to generate light of a wavelength which varies over time. The binocular OCT imaging system further comprises an interferometer having a reference arm, and a first sample arm comprising a first scanning module arranged to scan a first beam of the light across the region of the first eye and receive first reflected light that has been reflected by the region of the first eye as a result of the first beam being scanned across the region of the first eye by the first scanning module. The interferometer further comprises a second sample arm comprising a second scanning module arranged to scan a second beam of the light across the region of the second eye simultaneously with the scanning of the first beam across the region of the first eye by the first scanning module, the second scanning module being further arranged to receive second reflected light that has been reflected by the region of the second eye as a result of the second beam being scanned across the region of the second eye by the second scanning module. The binocular OCT imaging system further comprises a photodetector arranged to receive the first reflected light, the second reflected light, and reference light being light from the swept light source that is propagating along the reference arm, and generate an electrical signal having frequency components that comprise first frequency components arising from an interference between the first reflected light and the reference light, and second frequency components arising from an interference between the second reflected light and the reference light, the first frequency components spanning a first frequency band and the second frequency components spanning a second frequency band. A difference between an optical path length of the first sample arm and an optical path length of the second sample arm is such that at least a portion of the first frequency band does not overlap with the second frequency band, and at least a portion of the second frequency band does not overlap with the first frequency band. The binocular OCT imaging system further comprises a filter module arranged to filter the electrical signal by passing at least some of the first frequency components in the portion of the first frequency band that does not overlap with the second frequency band, and passing at least some of the second frequency components in the portion of the second frequency band that does not overlap with the first frequency band, and an OCT image data generating module arranged to generate, based on the at least some of the first frequency components passed by the filter module, first OCT image data representing the image of the region of the first eye, and to generate, based on the at least some of the second frequency components passed by the filter module, second OCT image data representing the image of the region of the second eye.

BRIEF DESCRIPTION OF THE DRAWINGS

Example embodiments will now be explained in detail, by way of non-limiting example only, with reference to the accompanying figures described below. Like reference numerals appearing in different ones of the figures can denote identical or functionally similar elements, unless indicated otherwise.

DETAILED DESCRIPTION OF EXAMPLE EMBODIMENTS

Figure 1:
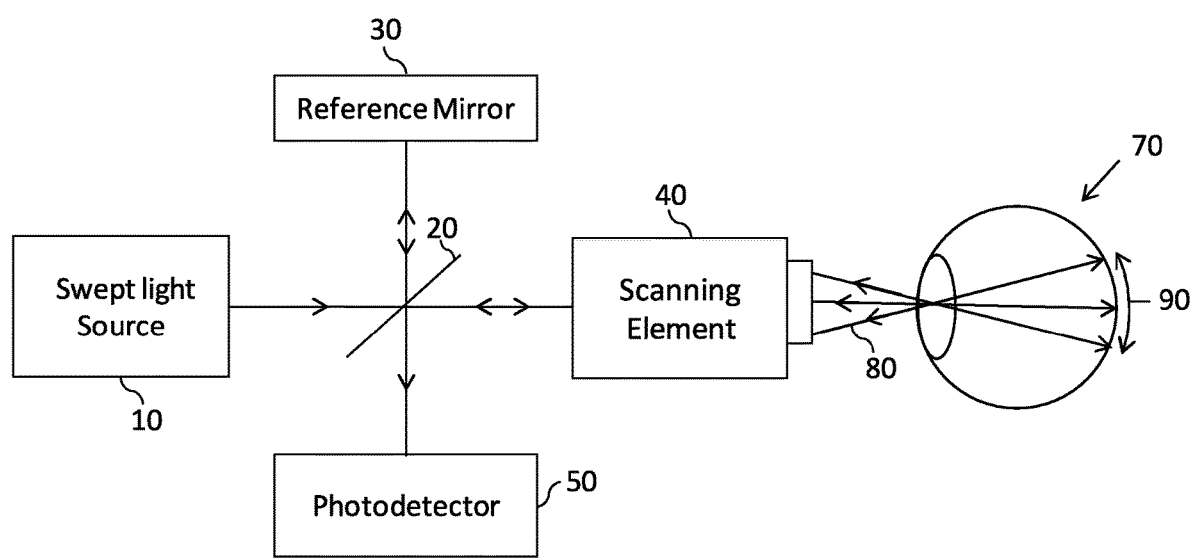
FIG. 1 is a schematic illustration of a conventional swept source OCT imaging system.
Figure 2A:
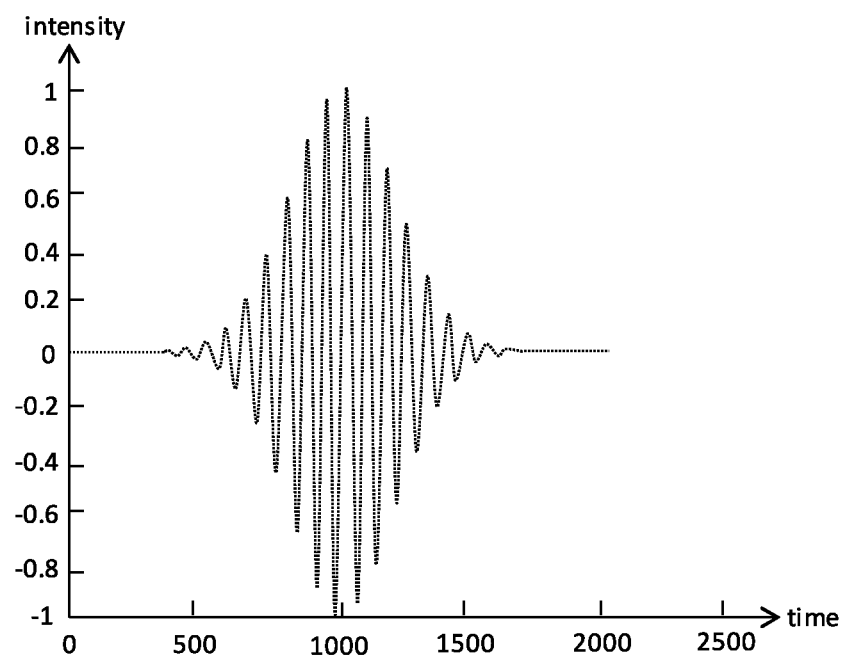
FIG. 2A is a schematic illustration of an interferogram generated by a photodetector of the ophthalmic swept-source OCT imaging system of FIG. 1.
Figure 2B:
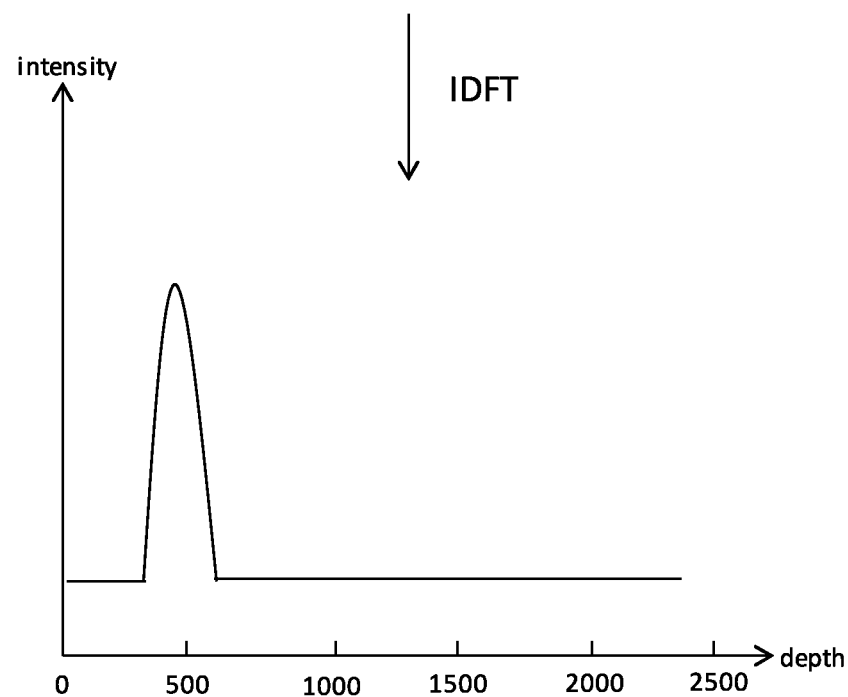
FIG. 2B is a schematic illustration of a depth profile of an eye determined from the interferogram of FIG. 2A.
Figure 3:
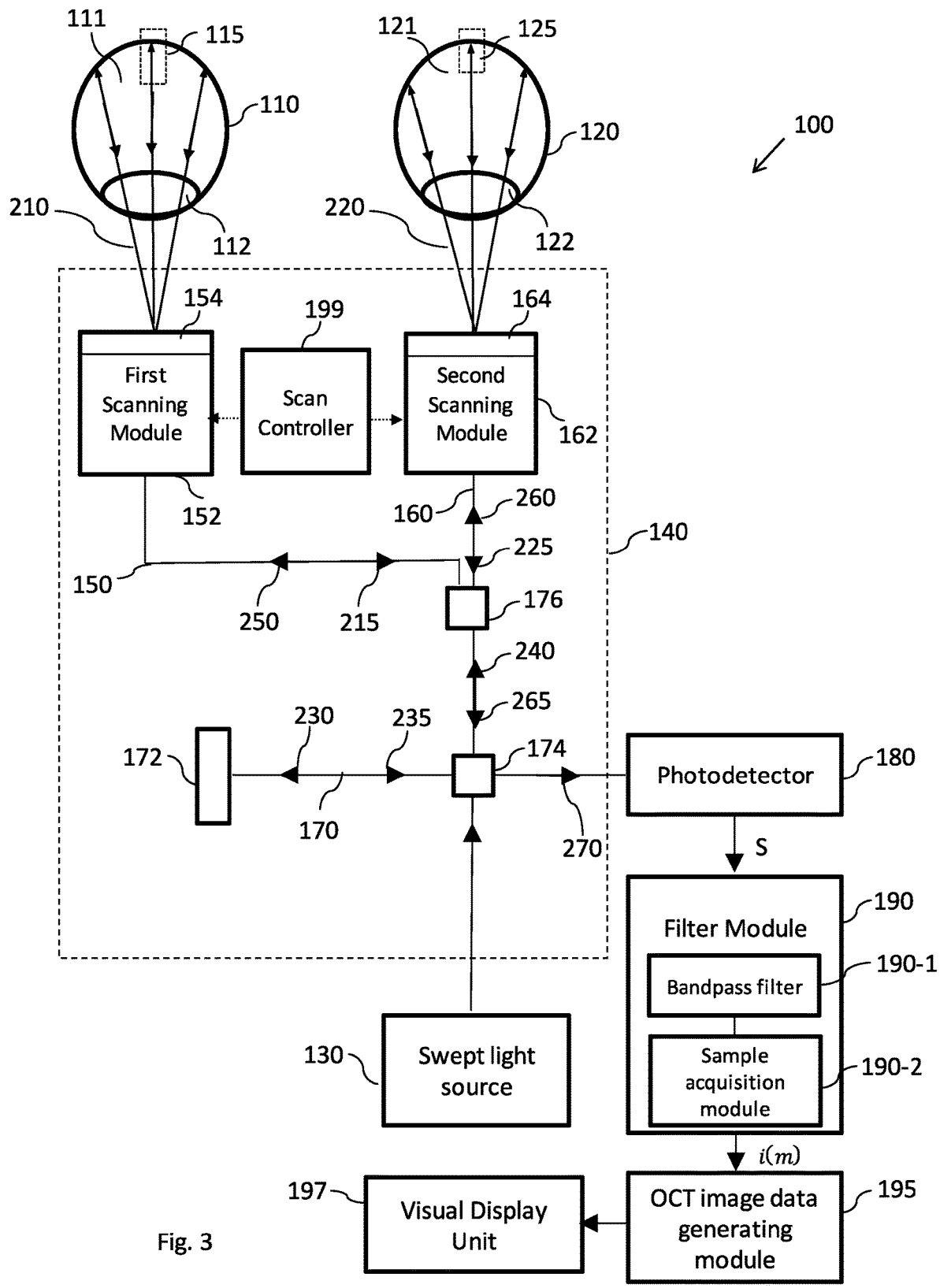
FIG. 3 is a schematic illustration of a binocular OCT imaging system in accordance with a first example embodiment herein.

FIG. 3 is a schematic illustration of a binocular OCT imaging system 100 for simultaneously imaging a region 115 of a first eye 110 of a subject and a region 125 of a second eye 120 of the subject, in accordance with a first example embodiment herein. The region 115 of the first eye 110 may, as in the present example embodiment, be in a posterior segment 111 of the first eye 110, but may alternatively be in an anterior segment 112 of the first eye 110. Furthermore, in the present example embodiment, the region 125 of the second eye 120 is a posterior segment 121 of the second eye 120, but the region 125 may alternatively be in an anterior segment 122 of the second eye 120.

In FIG. 3, the binocular OCT imaging system 100 comprises a swept light source 130 arranged to generate light of a wavelength which varies over time. The swept light source 130 may, as in the present example embodiment, be arranged to output substantially monochromatic light while the wavelength of the monochromatic light is swept across a range of wavelength values. The swept light source 130 may thus be arranged to output light whose wavelength/wavenumber changes over time. For example, denoting the wavenumber of the light output by the swept light source 130 at time t by k(t), the wavenumber k(t) may be swept linearly and can be written as $k(t)=k_0+\delta k \times t$, wherein $k_0$ is a starting wavenumber at the start of the sweep, and $\delta k = \Delta k/\Delta t$ is a rate at which the wavenumber of the output light is swept, wherein $\Delta k$ is the range over which the wavenumber changes during the sweep, and $\Delta t$ is the duration of the sweep. The linewidth of the swept light source 130 (i.e. a width, such as a full width at half-maximum (FWHM), of the spectrum of light generated by the swept light source 130) determines the coherence length of the light and therefore the imaging depth of the swept-source OCT imaging system 100, while the wavelength/wavenumber sweep range determines axial resolution.

The binocular OCT imaging system 100 in FIG. 3 further comprises an interferometer 140 having a first sample arm 150, a second sample arm 160, and a reference arm 170 having a reference mirror 172. The interferometer 140 may, as in the present example embodiment, be an optical fiber interferometer, wherein spans of optical fiber guide light propagating along the reference arm 170, the first sample arm 150 and the second sample arm 160 of the interferometer 140. However, the interferometer 140 may alternatively be provided in the form of a free-space interferometer, in which light propagates through air between optical elements.

In FIG. 3, the first sample arm 150 comprises a first scanning module 152 arranged to scan a first beam 210 of the light across the region 115 of the first eye 110 and receive first reflected light 215 that has been reflected by the region 115 of the first eye 110 as a result of the first beam 210 being scanned across the region 115 of the first eye 110 by the first scanning module 152. Furthermore, the second arm 160 comprises a second scanning module 162 arranged to scan a second beam 220 of the light across the region 125 of the second eye 120 simultaneously with the scanning of the first beam 210 across the region 115 of the first eye 110 by the first scanning module 152. The second scanning module 162 is further arranged to receive second reflected light 225 that has been reflected by the region 125 of the second eye 120 as a result of the second beam 220 being scanned across the region 125 of the second eye 120 by the second scanning module 162.

As shown in FIG. 3, the region 115 of the first eye 120 may, as in the present example, extend along a propagation direction of the first beam 210 of light incident on the first eye 110 during use of the binocular OCT imaging system 100 to image the region 115 of the first eye 110. Moreover, the region 125 of the second eye 120 may, as in the present example embodiment, extend along a propagation direction of the second beam 220 of light incident on the second eye 120 during use of the binocular OCT imaging system 100 to image the region 125 of the second eye 120. Furthermore, the region 115 of the first eye 110 and the region 125 of the second eye 120 may, as in the present example embodiment, substantially correspond the same part of each respective eye such as the retina, for example. Moreover, the region 115 of the first eye 110 may, as in the present example embodiment, be substantially the same thickness from the surface of a retina of the first eye 110 as the thickness of the region 125 of the second eye 120 from the surface of a retina of the second eye 120. However, it should be noted that region 115 and region 125 need not correspond to the same region of the eye and do not need to be of the same thickness.

Each of the first scanning module 152 and the second scanning module 162 may, as the present example embodiment, comprise a two-mirror scanner arrangement and a focusing element (not shown). The two-mirror scanner arrangement comprises an H-galvanometer mirror and a V-galvanometer mirror which are provided in an optical arrangement that serves to scan the light beam in a horizontal direction and a vertical direction into the eye 110 or 120 via the focusing element. It should be noted, however, that one or both of the first scanning module 152 and the second scanning module 162 take a different form known to those versed in the art, and may, for example, employ a scanning mechanism that employs one or more micro-electromechanical system (MEMS) scanners, for example. The focusing element is arranged to focus light received from the H-galvanometer mirror and the V-galvanometer mirror onto a target scan location in the eye. It should be noted, however, that the first scanning module 150 and the second scanning module 162 are not so limited, as each of these modules may alternatively comprise a single scanning mirror that is rotatable about two (e.g. orthogonal) axes. Furthermore, the binocular OCT imaging system 100 may, as in the present example embodiment, further comprise a focus adjustment module (not illustrated) that is arranged to adjust a respective focal point of the respective focusing element of the first scanning module 152 and the second scanning module 162.

In the present example embodiment, the two galvanometer mirrors in each of the first scanning module 152 and the second scanning module 162 may be rotated by respective actuation mechanisms, such as motors, so as to vary the optical path of the first beam 210 and second beam 220 and therefore vary the scan location within the first eye 110 and the scan location within the second eye 120 during imaging. In addition, the scan angle of the light beam scanned into each eye may, as in the present example embodiment, depend on the inclination angles ($\theta$, $\phi$) of the H-galvanometer mirror and the V-galvanometer mirror, wherein angle $\theta$ is an inclination angle of the H-galvanometer mirror and angle $\phi$ is an inclination angle of the V-galvanometer mirror. The inclination angles $\theta$ and $\phi$ respectively indicate the degree of rotation of the H-galvanometer mirror and the V-galvanometer mirror about their respective axes of rotation.

In FIG. 3, the binocular OCT imaging system 100 further comprises a photodetector 180 arranged to receive the first reflected light 215, the second reflected light 225, and reference light 235, the reference light 235 being light from the swept light source 130 that is propagating along the reference arm 170 (in this example configuration, after having been reflected by the reference mirror 172). The photodetector 180 is further arranged to generate an electrical signal S comprising frequency components that include first frequency components arising from an interference between the first reflected light 215 and the reference light 235, and second frequency components arising from an interference between the second reflected light 225 and the reference light 235. The first frequency components span a first frequency band and the second frequency components span a second frequency band. Furthermore, a difference between an optical path length of the first sample arm 150 and an optical path length of the second sample arm 160 is such that at least a portion of the first frequency band does not overlap with the second frequency band, and at least a portion of the second frequency band does not overlap with the first frequency band.

The photodetector 180 may, as in the present example embodiment, take the form of a balanced avalanche photodiode detector, but may alternatively take the form of any standard point detector. The photodetector 180 may, as in the present example embodiment, generate the electrical signal S based on the intensity of the interference light signal 270 detected by the photodetector 180. As an example, if the region 115 of the first eye 110 has N retinal layers, and the region 125 of the second eye 120 has M retinal layers, the photodetector current $I_D(k)$ of the photodetector 180 for wavenumber k can be denoted by:

$$I_D(k) \propto S(k)(\Sigma_{n=1}^{N}\sqrt{R_n R_R}(\cos 2kz_n) + \Sigma_{m=1}^{M}\sqrt{R_m R_R}(\cos 2kz_m)), \quad (1)$$

where S(k) is the optical power spectral density of the swept light source (130) defined as a function of wavenumber k of the light output by the swept light source, $R_n$ is the reflectivity of the n-th retinal layer of the first eye, $R_m$ is the reflectivity of the m-th retinal layer of the second eye 120, $R_R$ is the reflectivity of the reference arm 170, $z_n$ is a value representative of the optical path length difference between the reference arm 170 and the n-th retinal layer of the first eye 110, and $z_m$ is a value representative of the optical path length difference between the reference arm 170 and the m-th retinal layer of the second eye 120. Equation (1) thus denotes the detected intensity caused by interference between reflected light from the first eye 110, reflected light from the second eye 120, and the reflected light 235 in the reference arm 170. Due to the typically low reflectivity of the eye, interference between reflected light from the two eyes may be small in magnitude compared to the interference resulting from reference light in the reference arm 170.

In FIG. 3, the binocular OCT imaging system 100 further comprises a filter module 190 arranged to filter the electrical signal S by passing at least some of the first frequency components in the portion of the first frequency band that does not overlap with the second frequency band, and passing at least some of the second frequency components in the portion of the second frequency band that does not overlap with the first frequency band. The filter module 190 may, as in the present example embodiment, comprise a band-pass filter 190-1. Furthermore, the filter module 190 may further comprise, as in the present example embodiment, a sample acquisition module 190-2 arranged to acquire a set of samples i(m) of the filtered electrical signal, and more specifically, a set of samples of the at least some of the first frequency components and the at least some of the second frequency components. By appropriately setting an optical path difference between the first sample arm 150 and the second sample arm 160, the frequency components of the electrical signal S that are caused by reflection of light from retinal layers at the same depth within each respective eye are spaced apart along the frequency axis. Accordingly, setting a sufficient optical path difference between the first sample arm 150 and the second sample arm 160 effectively can allow reflectivity information for layers at the same depth within each eye to be simultaneously extracted.

In FIG. 3, the binocular OCT imaging system 100 also has an OCT image data generating module 195 that is arranged to generate, based on the at least some of the first frequency components passed by the filter module 190, first OCT image data representing the image of the region 115 of the first eye 110. The OCT image data generating module 195 is further arranged to generate, based on the at least some of the second frequency components passed by the filter module 190, second OCT image data representing the image of the region 125 of the second eye 120. The first OCT image data may, as in the present example embodiment, comprise a first A-scan of the region 115 of the first eye 110, and the second OCT image data may comprise a second A-scan of the region 125 of the second eye 120. Furthermore, the OCT data generating module 195 may, as in the present example embodiment, be arranged to generate the first A-scan and the second A-scan by performing inverse Fourier transform on the samples of the filtered electrical signal.

The binocular OCT imaging system 100 may, as in the present example embodiment, further comprise a visual display unit 197, which is arranged to display the image of the region 115 of the first eye 110 represented by the first OCT image data, and/or the image of the region of the second eye 120 represented by the second OCT image.

Figure 4:
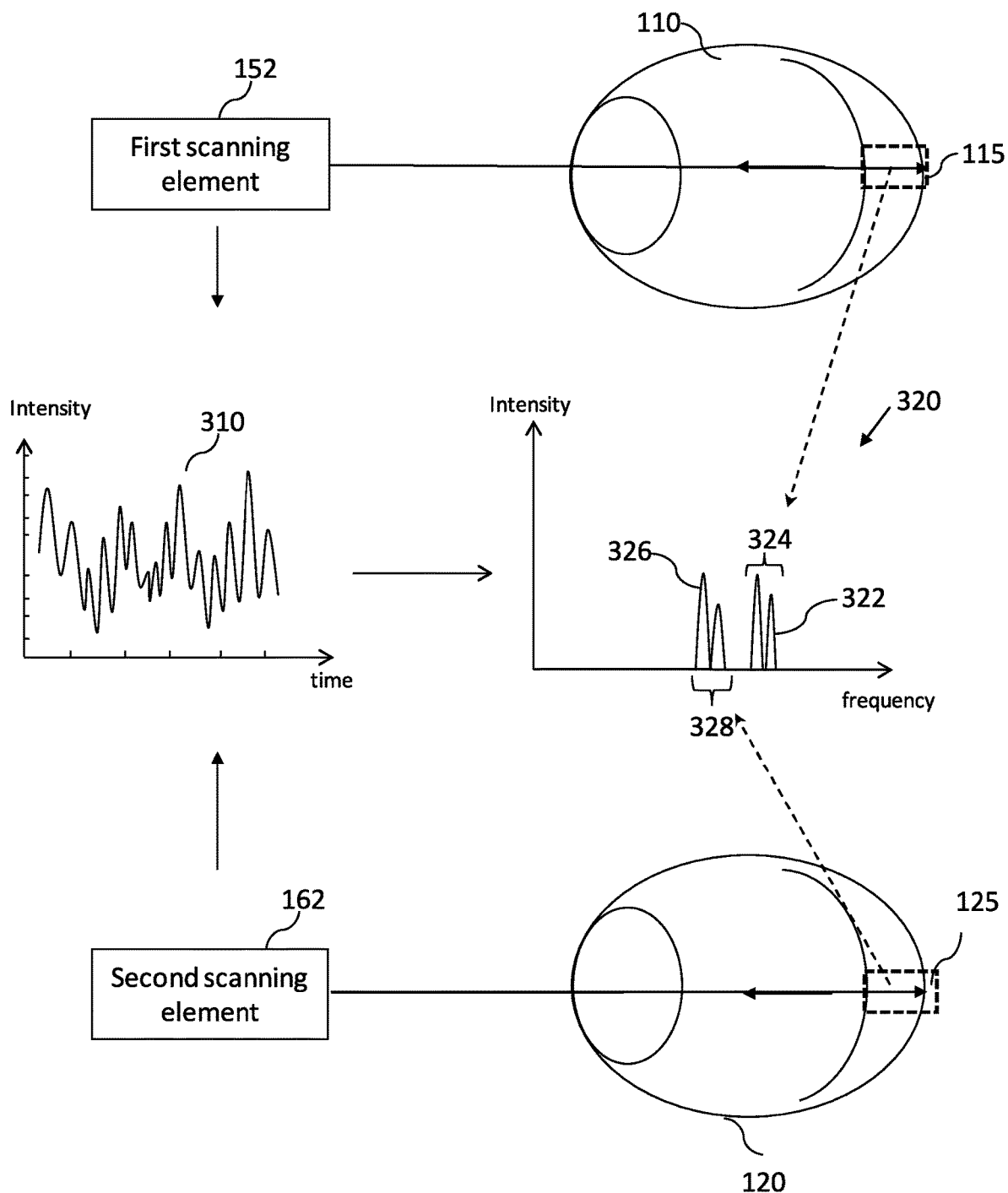
FIG. 4 illustrates first frequency components and second frequency components of an electrical signal generated by a photodetector of the binocular OCT imaging system of FIG. 3.

Referring to FIG. 4, schematic plot 310 illustrates how the electrical signal S that is generated by the photodetector 180 on the basis of the interference light 270 varies with the wavelength of the swept light source 130 during a sweep of the wavelength performed by the swept light source 130. Plot 320 in FIG. 4 illustrates frequency components of the electrical signal S, and is obtained by performing an inverse Fourier transform on the samples of the filtered electrical signal. As shown in plot 320, the first frequency components 322 (caused by interference of the light reflected from the region 115 of the first eye 110) of electrical signal S span the first frequency band 324, and the second frequency components 326 (caused by interference of the light reflected from region 125 of the second eye 120) of the electrical signal S span the second frequency band 328. FIG. 4 also represents the first scanning element 152 shown in association with the first eye 110, and the second scanning element 162 shown in association with the second eye 120.

In the example of FIG. 4, the difference between the optical path length of the first sample arm 150 and the optical path length of the second sample arm 160 is such that the first frequency band 324 does not overlap with the second frequency band 328. By ensuring the first frequency band 324 and the second frequency band 328 do not overlap, it may be possible to extract the first frequency components 322 and the second frequency components 326, thereby allowing to the entire reflectivity depth profile for each of the two regions 115 and 125 to be obtained.

Referring again to FIG. 3, the first sample arm 150 has a greater optical path length compared to the second sample arm 160 in the present example embodiment. To ensure that the first frequency band 324 and the second frequency band 328 do not overlap for the binocular OCT imaging system 100 of FIG. 3, the difference between the optical path length of the first sample arm 150 and the optical path length of the second sample arm 160 may, as in the present example embodiment, be equal to or greater than the length of the region 125 of the second eye 120, wherein the length of the region 125 of the second eye 120 is along a propagation direction of the second beam 220 of light incident on the second eye 120 during use of the binocular OCT imaging system 100 to image the region 125 of the second eye 120.

Furthermore, to ensure that the region 115 of the first eye 110 and the region 125 of the second eye 120 can be imaged in their entirety by the binocular OCT imaging system 100, the coherence length of the swept light source 130 may, as in the present example embodiment, be greater than a sum of a length of the region 115 of the first eye 110 and a length of the region 125 of the second eye 120. The length of the region 115 is along a propagation direction of the first beam 210 of light incident on the first eye 110 during use of the binocular OCT imaging system 100 to image the region 115 of the first eye 110. Furthermore, the length of the region 125 of the second eye 120 is along a propagation direction of the second beam 220 of light incident on the second eye 120 during use of the binocular OCT imaging system 100 to image the region 125 of the second eye 120. In addition, the coherence length of the swept light source 130 may, as in the present example embodiment, be greater than the difference between an optical path length of the first sample arm 150 and an optical path length of the second sample arm 160.

Although the difference in optical path length between the first sample arm 150 and the second sample arm 160 in the example of FIG. 3 is set such that first frequency band 324 and the second frequency band 328 do not overlap, it should be noted that, in an alternative example embodiment, the difference in optical path length between the first sample arm 150 and the second sample arm 160 may be such that there is some degree of overlap between the first frequency band 324 and the second frequency band 328. However, reflectivity information for at least a part of the region 115 of the first eye 110 and at least a part of the region 125 of the second eye 120 can be obtained as long as at least a portion of the first frequency band 324 does not overlap with the second frequency band 328, and at least a portion of the second frequency band 328 does not overlap with the first frequency band 324.

Figure 5:
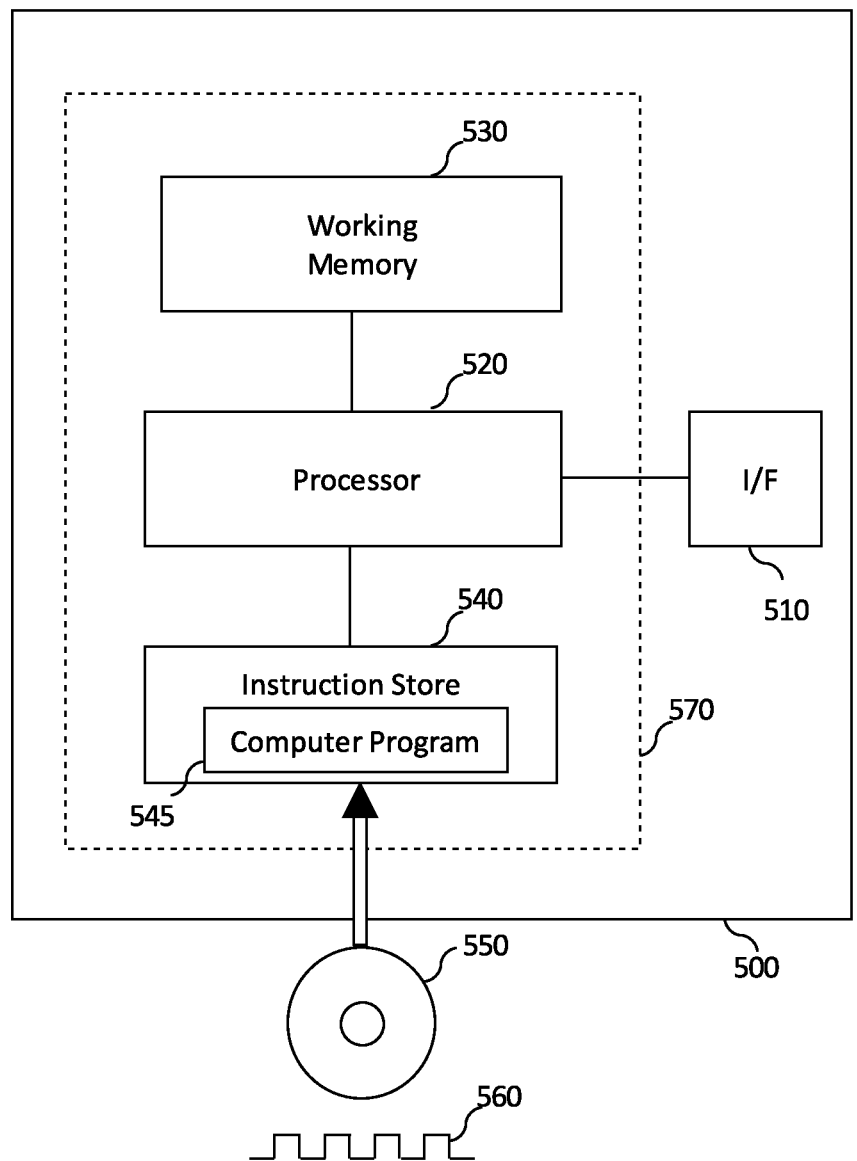
FIG. 5 illustrates an example hardware implementation of an OCT image data generating module of the binocular OCT imaging system in FIG. 3.

FIG. 5 shows an example implementation of a signal processing apparatus 500 of an example embodiment herein, in the form of programmable signal processing hardware. In one example embodiment herein, the signal processing apparatus 500 can form OCT image data generating module 195 of FIG. 3 (and/or of FIGS. 6-8). The signal processing apparatus 500 comprises an interface module 510 for receiving samples of the filtered electrical signal provided by the filter module 190, and for providing the first OCT image data and the second OCT image data to the virtual display unit 197. The signal processing apparatus 500 further comprises a processor (CPU) 520, a working memory 530 (e.g. a random-access memory) and an instruction store 540 storing a computer program 545 comprising computer-readable instructions which, when executed by the processor 520, cause the processor 520 to perform the processing operations of the apparatus OCT image data generating module 195. The instruction store 540 may comprise a ROM (e.g. in the form of an electrically-erasable programmable read-only memory (EEPROM) or flash memory) which is pre-loaded with the computer-readable instructions. Alternatively, the instruction store 540 may comprise a RAM or similar type of memory, and the computer-readable instructions can be input thereto from a computer program product, such as a computer-readable storage medium 550 such as a CD-ROM, etc. or a computer-readable signal 560 carrying the computer-readable instructions. In the present example embodiment, the combination 570 of the hardware components shown in FIG. 5, comprising the processor 520, the working memory 530 and the instruction store 540, is configured to perform functions of the OCT image data generating module 195.

Returning to the binocular OCT imaging system 100 of FIG. 3, the reference arm 170 may, as in the present example embodiment, further comprise a first optical coupler 174 arranged to split the light generated by the swept light source 130 into a first light 230 and a second light 240, and to direct the first light 230 to the reference mirror 172. The first sample arm 150 further comprises a second optical coupler 176, which is arranged to split the second light 240 into a third light 250 and a fourth light 260. The first scanning module 152 is arranged to scan a beam of the third light 250 across the region 115 of the first eye 110 and direct the first reflected light 215 to the second optical coupler 176. Furthermore, the second sample arm 160 further comprises the second optical coupler 176, the second scanning module 162 being arranged to scan a beam of the fourth light 260 across the region 125 of the second eye 120 and direct the second reflected light 225 to the second optical coupler 176. Furthermore, the second optical coupler 176 is arranged to combine the first reflected light 215 and the second reflected light 225 to generate a combined reflected light 265. The electrical signal S generated by the photodetector 180 is indicative of an interference between the combined reflected light 265 and the reference light (third reflected light) 235.

The first optical coupler 174 may, as in the present example embodiment, split the light generated by the swept light source 130 using an uneven split ratio such that the second light 240 (which is split into the third light 250 and the fourth light 260) is of higher optical power than the first light 230 directed to the reference mirror 172. For example, the first optical coupler 174 may employ a split ratio of 75:25, wherein 75% of the power of the light generated by the swept light source 130 is output as the first light 230, and 25% of the power of the light generated by the swept light source 130 is directed to the reference mirror 172. However, the first optical coupler 174 may, however, be arranged to split the generated light using another split ratio. In the present example embodiment, the second optical coupler 176 is a 1×2 optical coupler and has a 50:50 split ratio in order to deliver equal power to the first eye 110 and second eye 120. However, the second optical coupler 176 is not limited in this respect, and may employ a different split ratio.

The reference arm 170 of binocular OCT imaging system 100 in FIG. 3 comprises a single reference mirror 172. In this example embodiment, the first optical coupler 174 is further arranged to receive third reflected light 235 resulting from a reflection of the first light 230 by the reference mirror 172, and to generate an interference light 270 by combining the third reflected light 235 with the combined reflected light 265. The photodetector 180 is further arranged to receive the interference light 270.

The binocular OCT imaging system 100 in FIG. 3 may, as in the present example embodiment, further comprises a first shutter 154 provided in the first sample arm 150 that is operable to open and close, and a second shutter 164 provided in the second sample arm that is operable to open and close. The first shutter 154 is arranged to allow the first reflected light 215 to propagate to the photodetector 180 when the first shutter 154 is open, and to prevent the first reflected light 215 from propagating to the photodetector 180 when the first shutter 154 is closed, the photodetector 180 being arranged to receive the first reflected light 215 and generate the electrical signal S comprising the first frequency components 322 when the first shutter 154 is open. The second shutter 164 is arranged to allow the second reflected light 225 to propagate to the photodetector 180 when the second shutter 164 is open, and to prevent the second reflected light 225 from propagating to the photodetector 180 when the second shutter 164 is closed, the photodetector 180 being arranged to receive the second reflected light 225 and generate the electrical signal S comprising the second frequency components 326 when the second shutter 164 is open. Using a shutter in one or both of the sample arms in the manner described above allows each eye to be imaged individually without unnecessary exposure of the other eye to an imaging beam. This is advantageous when only one of the eyes need to be imaged.

As shown in FIG. 3, the binocular OCT imaging system 100 may further optionally comprise a scan controller 199, which is arranged to control the first scanning module 152 and the second scanning module 162 to synchronously perform scans using a common scan pattern. By using a common scan pattern, a common ocular region can be imaged simultaneously in both eyes, allowing faster image acquisition. However, in other example embodiments, the scan controller 199 may be arranged to independently control the first scanning module 152 and the second scanning module 162 to perform respective scans (with potentially different scan patterns) on different respective regions of the first eye 110 and the second eye 120.

Figure 6:
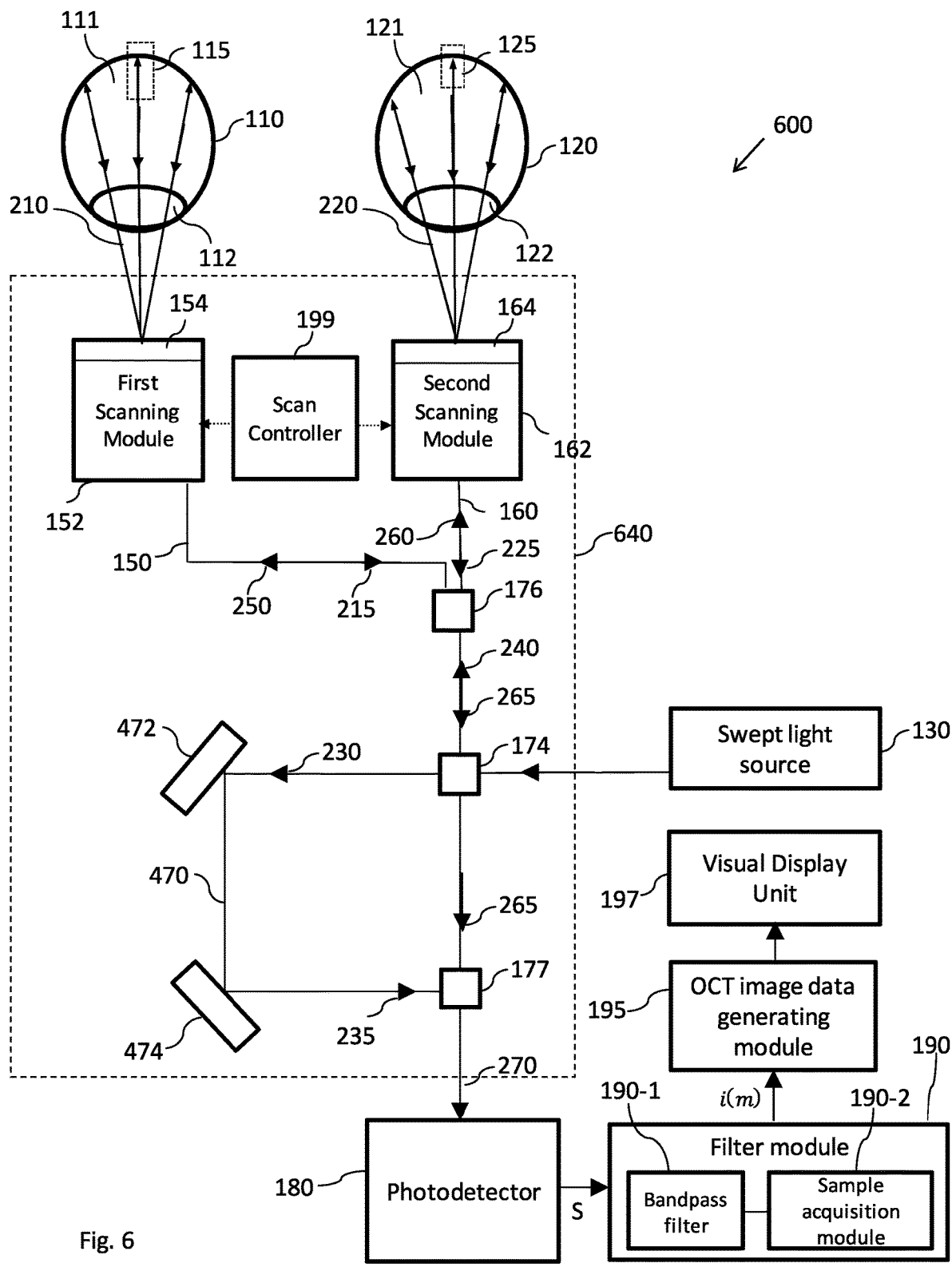
FIG. 6 is a schematic illustration of a binocular OCT imaging system in accordance with a second example embodiment herein.

Although the reference arm 170 in the embodiment of FIG. 3 comprises a single reference mirror 172, the reference arm 170 is not limited in this respect. As an example, FIG. 6 illustrates a binocular OCT imaging system 600 according to a second example embodiment, which is identical to the first example embodiment of FIG. 3 but has an alternative implementation of the reference arm. In FIG. 6, instead of a single reference mirror 172 as shown in FIG. 3, the reference arm 470 of the binocular OCT imaging system 600 comprises a first reference mirror 472 and a second reference mirror 474, the first reference mirror 472 being arranged to reflect the first light 230 from the first optical coupler 174 to the second reference mirror 474. Moreover, the binocular OCT imaging system 600 of the second example embodiment further comprises a third optical coupler 177 arranged to generate an interference light 270 by combining the combined reflected light 265 with third reflected light 235 which results from a reflection of the first light by the second reference mirror 474. The photodetector 180 is further arranged to receive the interference light 270.

Figure 7:
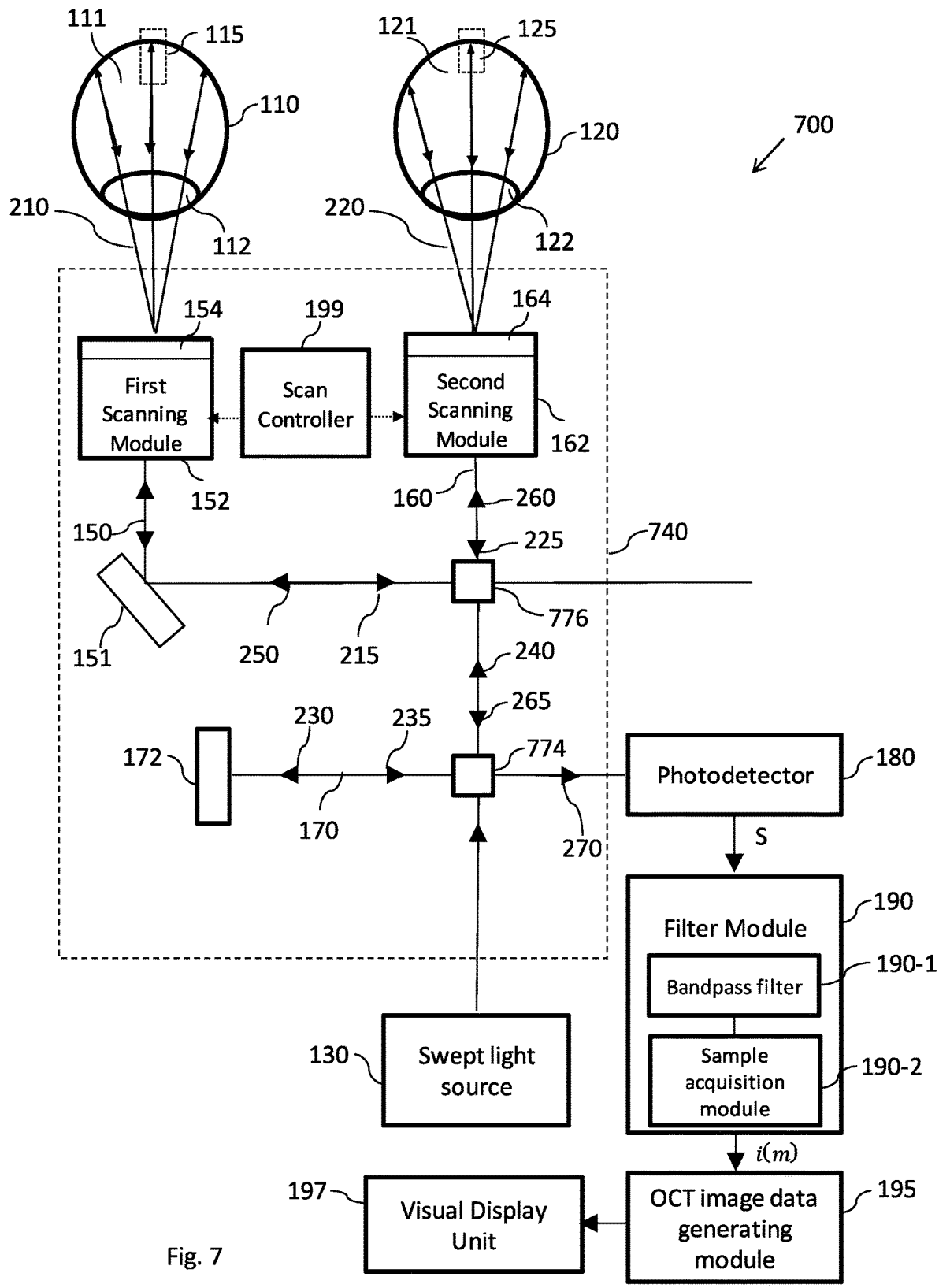
FIG. 7 is a schematic illustration of a binocular OCT imaging system in accordance with a third example embodiment herein.

FIG. 7 illustrates a binocular OCT imaging system 700 according to a third example embodiment, which comprises an interferometer 740 that is a free-space implementation of the interferometer 140 in the first example embodiment of FIG. 3. In the interferometer 740 of FIG. 7, the various lights described above with reference to FIG. 3 propagate in free space instead of through optical fibers. Furthermore, the first optical coupler 174 and the second optical coupler 176 are respectively replaced by a first free space beam splitter 774 and a second free space beam splitter 776, respectively. The first free space beam splitter 774 and the second free space beam splitter 776 in FIG. 7 are arranged to perform the same respective functions as those described for the first optical coupler 174 and the second optical coupler 176 in the fiber optic interferometer 140 of FIG. 3. In addition, in the interferometer 740 of FIG. 7, the first sample arm 150 further comprises a mirror 151 that arranged to guide the fourth light 250 to the second scanning module 162 and further guide the second reflected light 215 from the second scanning module 162 to the second free space beam splitter 776.

Figure 8:
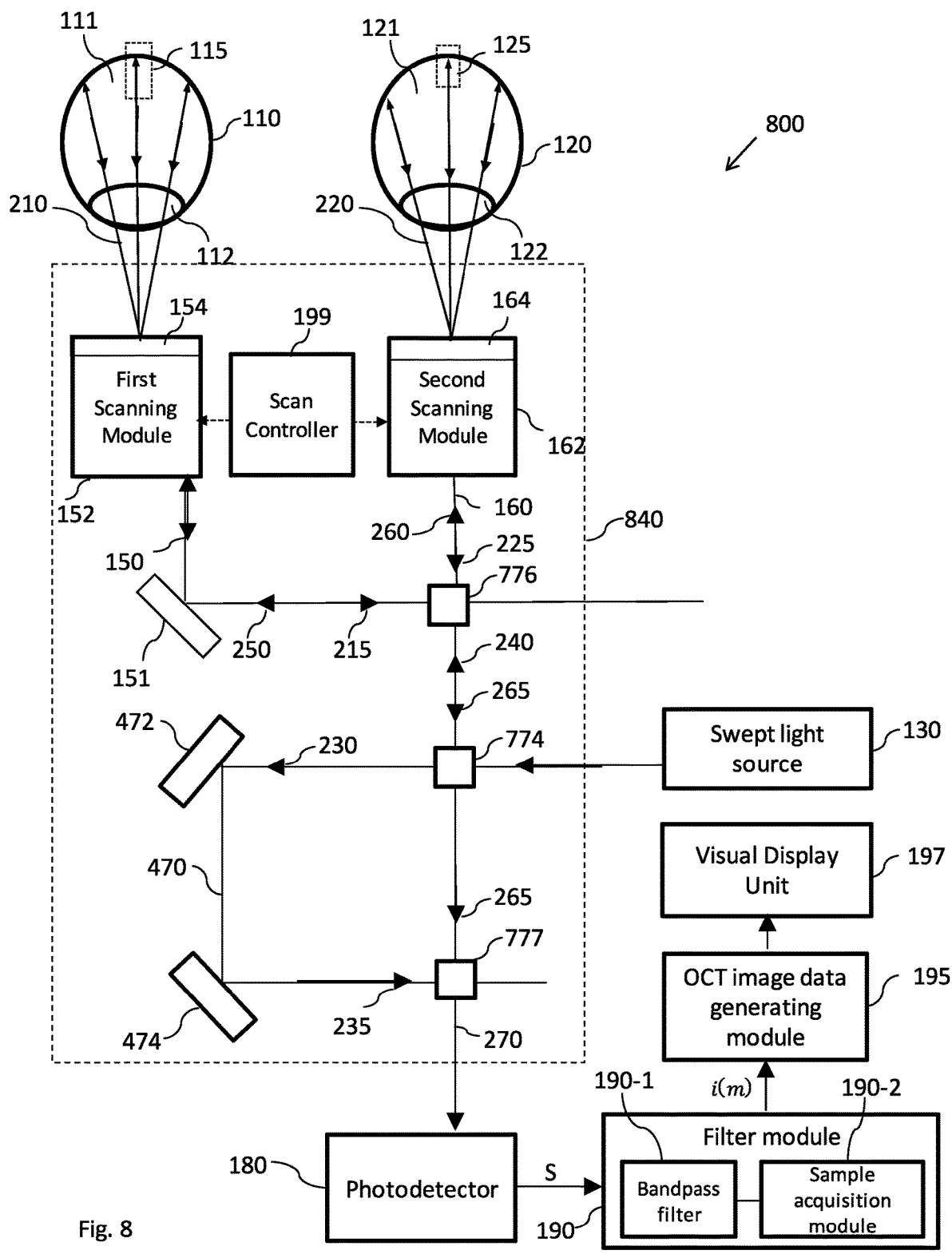
FIG. 8 illustrates a schematic illustration of a binocular OCT imaging system in accordance with a fourth example embodiment herein.

FIG. 8 illustrates a binocular OCT imaging system 800 according to a fourth example embodiment, which is identical to the binocular OCT imaging system 600 of the second example embodiment of FIG. 6, with the exception that binocular OCT imaging system 800 comprises an interferometer 840 that is the free space implementation of the fiber optic interferometer 640 in FIG. 6. In the interferometer 840 of FIG. 8, the optical couplers 176, 174, 177 of interferometer 640 in FIG. 6 are replaced by respective beam splitters 776, 774, 777 that are arranged to perform the same respective functions as the optical couplers in FIG. 6. In addition, as with the free-space implementation of FIG. 7, the first sample arm 150 of FIG. 8 also comprises a mirror 151 that is arranged to perform the same function as described for mirror 151 in FIG. 7.

Figure 9:
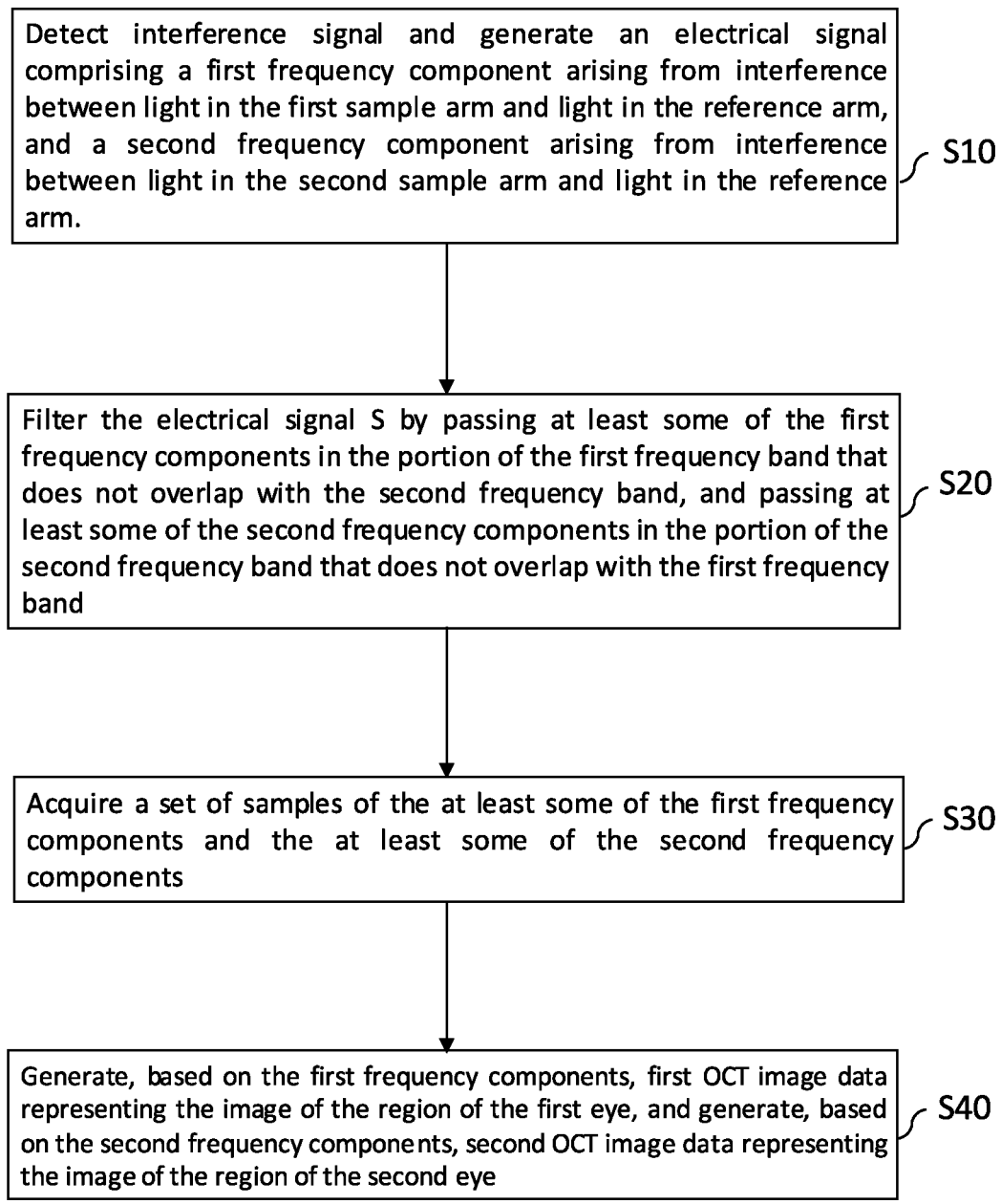
FIG. 9 is a flow diagram illustrating a process of acquiring an image of the first region of the first eye and an image of the second region of the second eye using the binocular OCT imaging system of any one of the example embodiments illustrated in FIGS. 3, 6, 7 and 8.

FIG. 9 illustrates a process of generating the first OCT image data representing an image of the region 115 of the first eye 110, and the second OCT image data representing an image of the region 125 of the second eye 120, using the binocular OCT imaging system 100 of FIG. 3. Although the process of FIG. 9 is described herein for purposes of illustration in the context of the system 100 of FIG. 3, it should be noted that the process of FIG. 9 is also applicable to (and is performed in the same manner for) any of the other example embodiments described herein, such as those of FIGS. 6-8.

In step S10 of FIG. 9, the photodetector 180 detects interference light 170 and generates an electrical signal S that comprises first frequency components 322 arising from interference between light in the first sample arm 150 and light in the reference arm 170, and second frequency components 326 arising from interference between light in the second sample arm 160 and light in the reference arm 170. A difference between an optical path length of the first sample arm 150 and an optical path length of the second sample arm 160 is such that at least a portion of the first frequency band 324 does not overlap with the second frequency band 328, and at least a portion of the second frequency band 328 does not overlap with the first frequency band 324. The electrical signal correlates detected intensity of the interference signal 170 against wavelength as the wavelength of the swept light source 130 is swept across its range of available optical frequencies.

In step S20 of FIG. 9, the filter module 190 filters the electrical signal S by passing at least some of the first frequency components 322 in the portion of the first frequency band 324 that does not overlap with the second frequency band 328, and passing at least some of the second frequency components 326 in the portion of the second frequency band 328 that does not overlap with the first frequency band 324. In the present example embodiment, the filter module 190 comprises a bandpass filter 190-1 and a sample acquisition module 190-2. The bandpass filter 190-1 may, as in the present example embodiment, be a tunable bandpass filter whose pass band is set by a controller (not shown) of the binocular OCT imaging system 100, for example, based on the location of region 115 of the first eye 110 and the location of the region 125 of the second eye 120.

The bandpass filter 190-1 may take on any suitable implementation, such as for example, a planar filter, a cavity filter, surface acoustic wave filter, passive LC filter, or an active filter. By using a tunable bandpass filter, the pass band of the bandpass filter 190-1 can be adjusted so that only frequency components caused by respective regions of interest in the first eye 110 and the second eye 120 are obtained. The adjustment of the pass band of the bandpass filter 190-1 can therefore be combined with the adjustment of the focal point of the respective focusing element of the first scanning module 152 and the second scanning module 162, to vary the respective locations of the regions in respective eyes are that are imaged. However, it should be noted that the bandpass filter 190-1 need not be a tunable bandpass filter, and can instead be a non-tunable bandpass filter having a fixed pass band. In implementations where a non-tunable bandpass filter is used, the location of the respective region in the first eye 110 and second eye 120 that is imaged by the binocular OCT imaging system 100 can be adjusted by changing the optical path length in the reference arm 170. Changing the optical path length of the reference arm in this way effectively shifts along the frequency axis the frequency components caused by a region of interest (in the axial direction/depth direction of the eye) to within the pass band of the bandpass filter 190-1.

It should be noted that, although the present example embodiment employs a single bandpass filter 190-1 to extract at least some of the first frequency components and at least some of the second frequency components, in other example embodiments, more than one bandpass filter can be employed to carry out this extraction. For example, a plurality of bandpass filters can be used in a filter bank arrangement, where each individual filter extracts a portion of the at least some of the first frequency components and the at least some of the second frequency components. Filtering a signal by dividing a target frequency band into sub-bands in this manner is advantageous in that lower sampling rate can be used for each sub-band when bandpass sampling is used.

In step S30 of FIG. 9, the filtered electrical signal output by the bandpass filter 190-1 is sampled by the sample acquisition module 190-2 to acquire a set of samples of the at least some of the first frequency components 322 passed by the filter module 190 and the at least some of the second frequency components 326 passed by the filter module 190. The sample acquisition module 190-2 may, as in the present example embodiment, acquire samples of the filtered electrical signal by bandpass sampling the filtered electrical signal. As an example, the frequency band of interest in the electrical signal S may comprise both the first frequency band 324 and the second frequency band 328. Accordingly, the sampling rate of the sample acquisition module 190-2 may be selected based on this frequency band of interest using the bandpass sampling theorem.

More specifically, for a frequency band of interest that has a center frequency $f_c$ and a bandwidth of B, band-pass sampling refers to the selection of a sampling rate $f_s$ in accordance with the following criteria:

$$\frac{2f_c - B}{n} \geq f_s \geq \frac{2f_c + B}{n+1} \quad (2)$$

wherein n is any positive integer that ensures the Shannon-Nyquist criterion of $f_s > 2B$ is satisfied for the selected sampling rate $f_s$. It should be noted that although equation (2) is presented using specific variables, it should be noted that the band-pass sampling theorem can also be presented differently using different variables (such as the upper bound and the lower bound of the frequency band which the band-pass signal spans) and still represent the same theorem.

Although the present example embodiment employs bandpass sampling to acquire samples of the filtered electrical signal, it should be noted that alternative sampling techniques may be used. For example, in some example embodiments, the filtered electrical signal can be heterodyned to an intermediate frequency before samples are acquired. Heterodyning a high-frequency signal to an intermediate frequency before sampling allows the sampling rate requirements of the sample acquisition module 190-2 to be significantly reduced. Furthermore, in other example embodiments, the sample acquisition module 190-2 may directly acquire samples of the filtered electrical signal in accordance with the Nyquist criterion, namely by selecting the sampling rate to be at least twice the maximum frequency in the frequency band of interest.

Denoting the filtered electrical signal over time as w(t), and the sampling rate of the sample acquisition module 190-2 as $f_s = 1/T_s$, where $T_s$ is the sampling interval, the sampled signal $I_s(t)$ is given by:

$$I_s(t) = w(t) \Sigma_{n=-\infty}^{\infty} \delta(t - nT_s) \quad (3)$$

In step S40 of FIG. 9, the OCT image data generating module 195 generates, based on the at least some of the first frequency components 322 passed by the filter module 190, first OCT image data representing the image of the region 115 of the first eye 110. The OCT image data generating module 195 further generates, based on at least some of the second frequency components 326 passed by the filter module 195, second OCT image data representing the image of the region 125 of the second eye 120.

The first OCT image data may, as in the present example embodiment, be a first A-scan of region 115 of the first eye 110. Furthermore, the second OCT image data may, as in the present example embodiment, be a second A-scan of the region 125 of the second eye 120. More specifically, the OCT image data generating module 195 may, as in the present example embodiment, generate the first A-scan and the second A-scan by first calculating an inverse Fourier transform of the samples $I_s(t)$ of the filtered electrical signal $S_F$ to generate A-scan data. In particular, for a SS-OCT imaging system, a reflection profile along the depth direction (axial direction) can be determined by the inverse Fourier transform of the detected electrical signal over wavenumber.

As an example, denoting the samples of the filtered electrical signal by i(m), m=0, 1, 2 ... M−1, the inverse Discrete Fourier Transform (IDFT) of the sequence of time-domain samples gives A-scan data that comprise a plurality of frequency domain data points which can be written as:

$$A(l) = \frac{1}{M} \sum_{m=0}^{M-1} i(m) e^{\frac{2\pi i l m}{M}} \quad (l = 0, 1, 2 \ldots M - 1) \quad (4)$$

wherein A(l) denotes the intensity value for the l-th frequency index. In the present example, as the output of the IDFT operation is complex-valued, only the magnitude of each A(l) value is taken to denote reflectivity information. For computational efficiency, OCT image data generating module 195 may, as in the present example embodiment, compute the IDFT of the samples i(m) using a Fast Fourier Transform algorithm.

As part of step S40, upon obtaining the A-scan data, the OCT image data generating module 195 may, as in the present example embodiment, generate the first A-scan representing the region 115 of the first eye 120, by mapping a first set of data points of the A-scan data to corresponding A-scan elements of the first A-scan, wherein each A-scan element of the A-scan represents a pixel of the A-scan. The amplitude of each data point mapped to an A-scan element may be understood to represent the intensity of the pixel represented by that A-scan element. In addition, the OCT data generating module 195 generates the second A-scan representing the region 125 of the second eye 120 by mapping a second set of data points of the A-scan data to corresponding A-scan elements of the second A-scan. In the present example, the optical path length of the first sample arm 150 is longer than the optical path length of the second sample arm 160 and therefore the higher frequency indices of the A-scan data correspond to the region 115 in the first eye 110 and are therefore mapped to A-scan elements of the first A-scan. Similarly, the lower frequency indices of the A-scan data correspond to the region 125 in the second eye 120 and are therefore mapped to A-scan data elements of the second A-scan. More generally, a predetermined mapping between frequency index and A-scan element may be used to map a data point of the A-scan data to an A-scan element of either the first A-scan (corresponding to the first eye 110) or the second A-scan (corresponding to the second eye 120).

Figure 10:
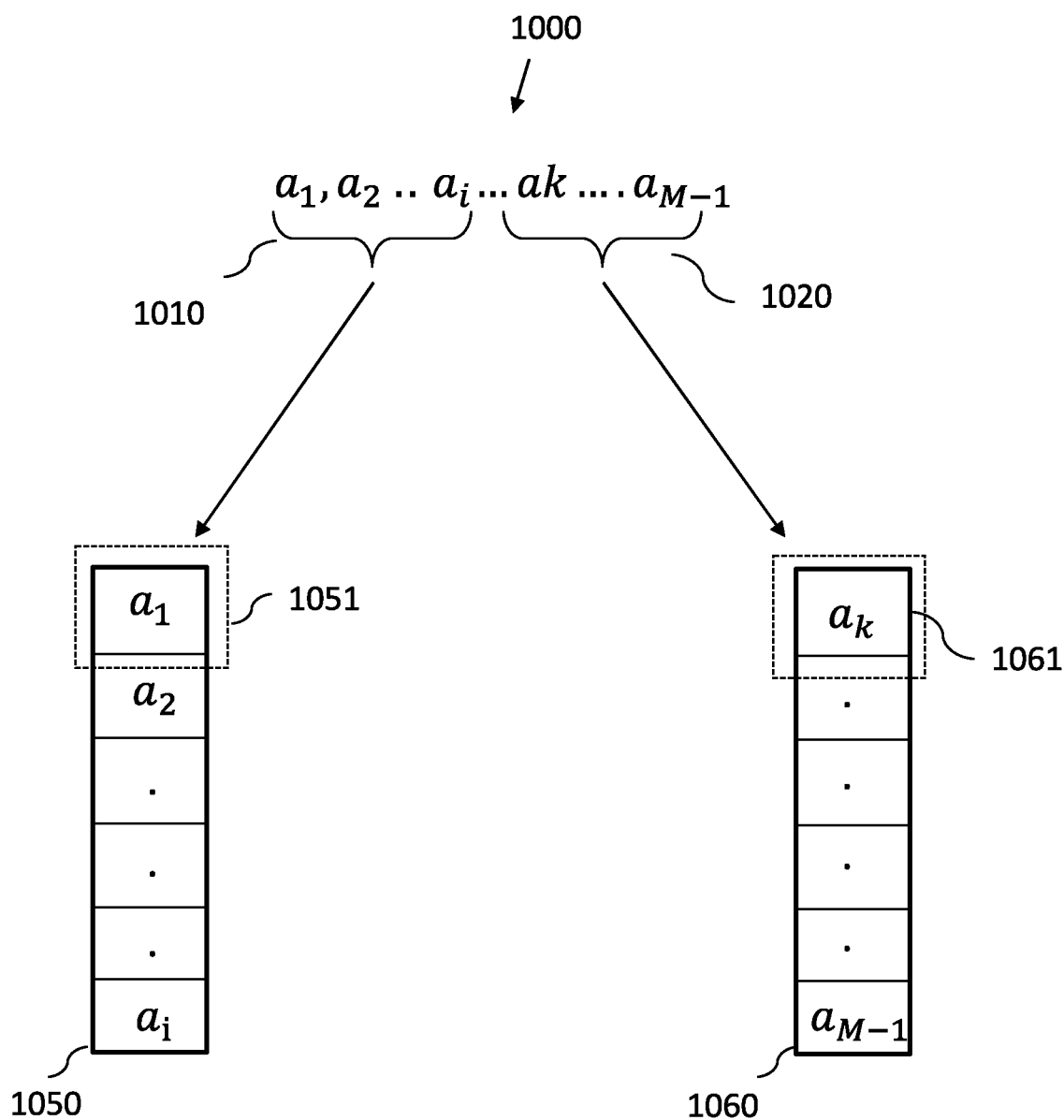
FIG. 10 illustrates a mapping of A-scan data to an A-scan of the region of the first eye, and an A-scan of the region of the second eye, in accordance with an example embodiment.

FIG. 10 illustrates a mapping of a first set 1010 of data points $a_1, a_2 \ldots a_i$ of A-scan data 1000 to A-scan elements of a first A-scan 1050, and a mapping of a second set 1020 of data points $a_k, \ldots a_{M-1}$ of the A-scan data 1000 to A-scan elements of a second A-scan 1060. The first A-scan 1050 represents the region 115 of the first eye 110, while the second A-scan 1060 represents the region 125 of the second eye 120. It should be noted, however, that not every frequency index of the A-scan data 1000 needs to be mapped to the first A-scan or the second A-scan. For example, in example embodiments where a frequency spacing exists between the first frequency band and the second frequency band, the frequency indices corresponding to the frequency spacing neither represent the region 115 of the first eye 110 nor the region 125 of the second eye 120. Accordingly, the A-scan data points for these frequency indices are not mapped to any of the A-scans.

In the present example embodiment, the first scanning module 152 is arranged to scan the first beam 210 of light across a plurality of regions of the first eye 110 by varying its scan angles (θ, φ), and the second scanning module 162 is arranged to scan the second beam of light across a plurality of regions of the second eye 120 by varying its scan angles (θ, φ). Furthermore, the scan controller 199 of the binocular OCT imaging system (100) is arranged to control the first scanning module 152 and the second scanning module 162 to synchronously perform scans using a common scan pattern. For example, the binocular OCT imaging system 100 may, as in the present example embodiment, synchronously vary the respective scan angles (θ, φ) of the first scanning module 152 and the second scanning module 162 during the simultaneous imaging of the first eye 110 and the second eye 120.

The OCT image data generating module 195 may, as in the present example, further generate a plurality of first A-scans corresponding to the plurality of regions of the first eye 110 and generate a plurality of second A-scans corresponding to the plurality of regions for the second eye 120. More specifically, the OCT image data generating module 195 may generate A-scan data corresponding to each value of the scan angle pair (θ, φ) based on the obtained values of the electrical signal S generated by the photodetector 180 when the first scanning module 152 and the second scanning module 162 respectively scan the first eye 110 and the second eye 120 using the value of the scan angle (θ, φ). In addition, the OCT image data generating module 195 may further perform, for A-scan data associated with each value of the scan angle (θ, φ) a mapping of a first set of data points of the A-scan data to corresponding A-scan elements of an A-scan of the first eye 110. In addition, the OCT image data generating module 195 may perform, for each A-scan data associated with each value of the scan angle (θ, φ), a mapping of a second set of datapoints of A-scan data to corresponding A-scan elements of an A-scan of the second eye 120.

Upon generating the plurality of first A-scans corresponding to the plurality of scan locations in the scanned region 115 of the first eye 110 and plurality of second A-scans corresponding to the plurality of scan locations in the scanned region 125 of the second eye 120, the OCT data generating module 195 may further array the plurality of first A-scans to form a first array of the A-scans that represent an image of the region 115 of the first eye 110. Furthermore, the OCT data generating module 195 may array the plurality of second A-scans to form a second array of the A-scans representing an image of the region 125 of the second eye 120. The first array and the second array may, as in the present example embodiment, be a two-dimensional array constituting a B-scan, although a three-dimensional array constituting a C-scan may be similarly formed.

Although the above example describes the binocular OCT imaging system 100 acquiring a plurality of A-scans for each eye by scanning the first scanning module 152 and the second scanning module 162 using a common scan pattern, it should be understood that the scan controller 199 may alternatively independently control the first scanning module 152 and the second scanning module 162 to perform respective scans (with potential different scan patterns) on different respective regions of the first eye 110 and the second eye 120. In an alternative example embodiment, as the two scanning modules use different scan angles during the obtaining of an electrical signal (measured intensity against wavelength for the full range of wavelength swept by swept light source 130), the OCT image data generating module 195 may map data points of the corresponding A-scan data (derived from the electrical signal S) to respective A-scans of the first eye 110 and the second eye 120 based on the respective scan angles used to obtain the electrical signal S. In other words, after obtaining A-scan data by performing inverse Fourier transform on the filtered electrical signal, a first set of data points are mapped to an A-scan of the first eye based on the scanning angle of the first scanning module 152 that was used to obtain the electrical signal. Furthermore, a second set of data points of the A-scan are mapped to an A-scan of the second eye based on the scanning angle of the second scanning module 162 that was used to obtain the electrical signal.

The example aspects described herein avoid limitations, at least some of which are specifically rooted in computer technology, relating to conventional OCT imaging systems that capture an OCT images one eye at a time, and which can have a slow overall image acquisition process, and with conventional OCT imaging systems that can simultaneously capture OCT images of both eyes but while requiring duplication of imaging hardware and high imaging system cost. By virtue of the example aspects described herein, for example, long coherence length of a swept light source used in a swept source OCT imaging system is exploited to devise a binocular OCT imaging system that is capable of imaging both eyes in one single OCT capture using fewer components than conventional binocular OCT imaging systems of the kind mentioned above and, in particular, using a single photodetector and a single reference arm. By virtue of the capabilities of the example aspects described herein, at least some of which are rooted in computer technology, the example aspects described herein improve computer processing, and also improve the field(s) of medical imaging and medical devices, in addition to OCT imaging systems.

In the foregoing description, example aspects are described with reference to several example embodiments. Accordingly, the specification should be regarded as illustrative, rather than restrictive. Similarly, the figures illustrated in the drawings, which highlight the functionality and advantages of the example embodiments, are presented for example purposes only. The architecture of the example embodiments is sufficiently flexible and configurable, such that it may be utilized in ways other than those shown in the accompanying figures.

Software embodiments of the examples presented herein may be provided as, a computer program, or software, such as one or more programs having instructions or sequences of instructions, included or stored in an article of manufacture such as a machine-accessible or machine-readable medium, an instruction store, or computer-readable storage device, each of which can be non-transitory, in one example embodiment. The program or instructions on the non-transitory machine-accessible medium, machine-readable medium, instruction store, or computer-readable storage device, may be used to program a computer system or other electronic device. The machine- or computer-readable medium, instruction store, and storage device may include, but are not limited to, floppy diskettes, optical disks, and magneto-optical disks or other types of media/machine-readable medium/instruction store/storage device suitable for storing or transmitting electronic instructions. The techniques described herein are not limited to any particular software configuration. They may find applicability in any computing or processing environment. The terms "computer-readable", "machine-accessible medium", "machine-readable medium", "instruction store", and "computer-readable storage device" used herein shall include any medium that is capable of storing, encoding, or transmitting instructions or a sequence of instructions for execution by the machine, computer, or computer processor and that causes the machine/computer/computer processor to perform any one of the methods described herein. Furthermore, it is common in the art to speak of software, in one form or another (e.g., program, procedure, process, application, module, unit, logic, and so on), as taking an action or causing a result. Such expressions are merely a shorthand way of stating that the execution of the software by a processing system causes the processor to perform an action to produce a result.

Some embodiments may also be implemented by the preparation of application-specific integrated circuits, field-programmable gate arrays, or by interconnecting an appropriate network of conventional component circuits.

Some embodiments include a computer program product. The computer program product may be a storage medium or media, instruction store(s), or storage device(s), having instructions stored thereon or therein which can be used to control, or cause, a computer or computer processor to perform any of the procedures of the example embodiments described herein. The storage medium/instruction store/storage device may include, by example and without limitation, an optical disc, a ROM, a RAM, an EPROM, an EEPROM, a DRAM, a VRAM, a flash memory, a flash card, a magnetic card, an optical card, nanosystems, a molecular memory integrated circuit, a RAID, remote data storage/archive/warehousing, and/or any other type of device suitable for storing instructions and/or data.

Stored on any one of the computer-readable medium or media, instruction store(s), or storage device(s), some implementations include software for controlling both the hardware of the system and for enabling the system or microprocessor to interact with a human user or other mechanism utilizing the results of the example embodiments described herein. Such software may include without limitation device drivers, operating systems, and user applications. Ultimately, such computer-readable media or storage device(s) further include software for performing example aspects of the invention, as described above.

Included in the programming and/or software of the system are software modules for implementing the procedures described herein. In some example embodiments herein, a module includes software, although in other example embodiments herein, a module includes hardware, or a combination of hardware and software.

While various example embodiments of the present invention have been described above, it should be understood that they have been presented by way of example, and not limitation. It will be apparent to persons skilled in the relevant art(s) that various changes in form and detail can be made therein. Thus, the present invention should not be limited by any of the above described example embodiments, but should be defined only in accordance with the following claims and their equivalents.

Further, the purpose of the Abstract is to enable the Patent Office and the public generally, and especially the scientists, engineers and practitioners in the art who are not familiar with patent or legal terms or phraseology, to determine quickly from a cursory inspection the nature and essence of the technical disclosure of the application. The Abstract is not intended to be limiting as to the scope of the example embodiments presented herein in any way. It is also to be understood that any procedures recited in the claims need not be performed in the order presented.

While this specification contains many specific embodiment details, these should not be construed as limitations on the scope of any inventions or of what may be claimed, but rather as descriptions of features specific to particular embodiments described herein. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

In certain circumstances, multitasking and parallel processing may be advantageous. Moreover, the separation of various components in the embodiments described above should not be understood as requiring such separation in all embodiments, and it should be understood that the described program components and systems can generally be integrated together in a single software product or packaged into multiple software products.

Having now described some illustrative embodiments and embodiments, it is apparent that the foregoing is illustrative and not limiting, having been presented by way of example. In particular, although many of the examples presented herein involve specific combinations of apparatus or software elements, those elements may be combined in other ways to accomplish the same objectives. Acts, elements and features discussed only in connection with one embodiment are not intended to be excluded from a similar role in other embodiments or embodiments.

The apparatuses described herein may be embodied in other specific forms without departing from the characteristics thereof. The foregoing embodiments are illustrative rather than limiting of the described systems and methods. Scope of the apparatuses described herein is thus indicated by the appended claims, rather than the foregoing description, and changes that come within the meaning and range of equivalence of the claims are embraced therein.

The invention claimed is:

1. A binocular optical coherence tomography, OCT, imaging system for simultaneously imaging a region of a first eye of a subject and a region of a second eye of the subject, the binocular OCT imaging system comprising:
a swept light source arranged to generate light of a wavelength which varies over time;
an interferometer comprising:
a reference arm;
a first sample arm comprising a first scanning module arranged to scan a first beam of the light across the region of the first eye and receive first reflected light that has been reflected by the region of the first eye as a result of the first beam being scanned across the region of the first eye by the first scanning module;
a second sample arm comprising a second scanning module arranged to scan a second beam of the light across the region of the second eye simultaneously with the scanning of the first beam across the region of the first eye by the first scanning module, the second scanning module being further arranged to receive second reflected light that has been reflected by the region of the second eye as a result of the second beam being scanned across the region of the second eye by the second scanning module;
a photodetector arranged to receive the first reflected light, the second reflected light, and reference light being light from the swept light source that is propagating along the reference arm, and generate an electrical signal(S) having frequency components that comprise first frequency components arising from an interference between the first reflected light and the reference light, and second frequency components arising from an interference between the second reflected light and the reference light, the first frequency components spanning a first frequency band and the second frequency components spanning a second frequency band, wherein a difference between an optical path length of the first sample arm and an optical path length of the second sample arm is such that at least a portion of the first frequency band does not overlap with the second frequency band, and at least a portion of the second frequency band does not overlap with the first frequency band;

a filter module arranged to filter the electrical signal(S) by passing at least some of the first frequency components in the portion of the first frequency band that does not overlap with the second frequency band and passing at least some of the second frequency components in the portion of the second frequency band that does not overlap with the first frequency band;

an OCT image data generating module arranged to generate, based on the at least some of the first frequency components passed by the filter module, first OCT image data representing the image of the region of the first eye, and to generate, based on the at least some of the second frequency components passed by the filter module, second OCT image data representing the image of the region of the second eye.

2. The binocular OCT imaging system according to claim 1, wherein the reference arm comprises at least one reference mirror and a first beam splitter arranged to split the light generated by the swept light source into a first light and a second light, and to direct the first light to the at least one reference mirror, the first sample arm further comprises a second beam splitter which is arranged to split the second light into a third light and a fourth light, the first scanning module being arranged to scan a beam of the third light across the region of the first eye and direct the first reflected light to the second beam splitter, the second sample arm further comprises the second beam splitter, the second scanning module being arranged to scan a beam of the fourth light across the region of the second eye and direct the second reflected light to the second beam splitter, the second beam splitter is further arranged to combine the first reflected light and the second reflected light to generate a combined reflected light, and the electrical signal(S) generated by the photodetector is indicative of an interference between the combined reflected light and the reference light.

3. The binocular OCT imaging system according to claim 2, wherein the reference arm comprises a single reference mirror, the first beam splitter is further arranged to receive third reflected light resulting from a reflection of the first light by the reference mirror and to generate an interference light by combining the third reflected light with the combined reflected light, the photodetector being arranged to receive the interference light.

4. The binocular OCT imaging system according to claim 1, wherein the interferometer is an optical fiber interferometer wherein spans of optical fiber guide light propagating along the reference arm, the first sample arm and the second sample arm of the interferometer.

5. The binocular OCT imaging system according to claim 1, wherein the region of the first eye is in one of an anterior segment or a posterior segment of the first eye, and the region of the second eye is in one of an anterior segment or a posterior segment of the second eye.

6. The binocular OCT imaging system according to claim 1, wherein the photodetector comprises a balanced avalanche photodiode detector.

7. The binocular OCT imaging system according to claim 1, further comprising a visual display unit arranged to display at least one of the image of the region of the first eye represented by the first OCT image data or the image of the region of the second eye represented by the second OCT image data.

8. The binocular OCT imaging system according to claim 1, further comprising at least one of:

a first shutter provided in the first sample arm and operable to open and close, the first shutter being arranged to allow the first reflected light to propagate to the photodetector when the first shutter is open, and to prevent the first reflected light from propagating to the photodetector when the first shutter is closed, the photodetector being arranged to receive the first reflected light and generate the electrical signal(S) comprising the first frequency components when the first shutter is open; or a second shutter provided in the second sample arm and operable to open and close, the second shutter being arranged to allow the second reflected light to propagate to the photodetector when the second shutter is open, and to prevent the second reflected light from propagating to the photodetector when the second shutter is closed, the photodetector being arranged to receive the second reflected light and generate the electrical signal(S) comprising the second frequency components when the second shutter is open.

9. The binocular OCT imaging system according to claim 1, further comprising a scan controller arranged to synchronously control the first scanning module according to a scan pattern and the second scanning module according to the scan pattern, thereby synchronously performing scans using the first scanning module and the second scanning module using the common scan pattern.

10. The binocular OCT imaging system according to claim 1, further comprising a scan controller arranged to independently control the first scanning module and the second scanning module to perform respective scans on different respective regions of the first eye and the second eye.

* * * * *